United States Patent [19]

Lascar et al.

[11] Patent Number: 4,834,714
[45] Date of Patent: May 30, 1989

[54] DOUBLE COMPARTMENT SYRINGE

[76] Inventors: Marcel Lascar, 10 Rue de la Vrilliere, Paris 75001; Jacques Charpentier, 1 Rue du Sanitas, Pithiviers 45300, both of France

[21] Appl. No.: 105,430
[22] PCT Filed: Nov. 10, 1986
[86] PCT No.: PCT/FR86/00380
§ 371 Date: Sep. 14, 1987
§ 102(e) Date: Sep. 14, 1987
[87] PCT Pub. No.: WO87/02896
PCT Pub. Date: May 21, 1987

[30] Foreign Application Priority Data

Nov. 14, 1985 [FR] France ................................ 85 17108

[51] Int. Cl.⁴ .............................................. A61M 5/08
[52] U.S. Cl. ...................................... 604/191; 604/85; 222/135
[58] Field of Search ............... 604/191, 187, 181, 183, 604/184, 186, 218, 226, 228, 125, 85; 222/330, 331, 135, 136

[56] References Cited

U.S. PATENT DOCUMENTS

| 1,234,582 | 7/1916 | Trueblood | 604/191 |
| 1,600,587 | 9/1926 | Hein | 604/183 |
| 2,841,145 | 7/1958 | Epps | 222/135 |
| 2,939,459 | 6/1960 | Lazarte et al. | 604/191 |
| 3,437,242 | 4/1966 | Poitras | 222/135 |
| 3,749,084 | 7/1973 | Cucchiar | 604/191 |
| 4,029,236 | 6/1977 | Carson et al. | 222/135 |
| 4,050,612 | 9/1977 | Stone | 222/135 |
| 4,220,261 | 9/1980 | White | 222/135 |
| 4,655,747 | 4/1987 | Allen | 604/191 |

FOREIGN PATENT DOCUMENTS

| 2848433 | 11/1977 | Fed. Rep. of Germany | 604/184 |
| 8400011 | 1/1984 | France | 604/187 |
| 8401291 | 4/1984 | U.S.S.R. | 604/187 |
| 0005503 | of 1912 | United Kingdom | 604/184 |

Primary Examiner—C. Fred Rosenbaum
Assistant Examiner—Mark O. Polutta
Attorney, Agent, or Firm—Lowe, Price, LeBlanc, Becker & Shur

[57] ABSTRACT

The desired invention concerns a syringe with a double compartment. The first compartment (10) is bounded by a first cylinder (12), closed off at one end by a first partition (13) in which an opening (15) is provided, and at its other end by a first sliding piston (14). This syringe also contains a second cylinder (17) coaxial to and inside of the first cylinder, attached at its first extremity to the first piston and closed of at its second extremity by a second partition (18), and an axial rod (16), coaxial to and inside of the secnd cylinder, that is attached to the first partition by its first extremity, sliding across the first piston (14) and supporting at its other extremity a second piston (19) that slides into the second cylinder. In this manner, a second compartment is formed by the second cylinder, the second piston, and the second partition, the volumes contained in the two compartments fluctuating simultaneously when the second cylinder is shifted in relation to the first one.

11 Claims, 5 Drawing Sheets

DOUBLE COMPARTMENT SYRINGE

The present invention relates to a syringe for medical use.

Figure 1:
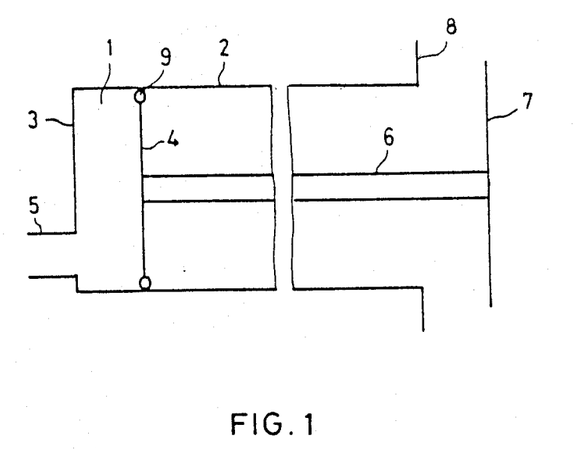
FIG. 1 is an extremely schematic representation of a conventional syringe as above-described.

FIG. 1 schematically shows a conventional syringe for medical use. This syringe includes a compartment 1 into which the liquid to be injected is introduced. This compartment is bordered by an exterior cylinder 2, by a partition 3 that closes off the cylinder at its first extremity, and by a piston 4 that slides into the cylinder 2. In the partition 3 is provided an opening with a tip 5 to which the needle or catheter to be used for injection or sample taking is attached.

In order to operate the syringe, an axial rod 6 is attached to the piston 4, the extremity of this rod being linked to either a circular plate or flanges 7, the flanges 8 being also provided at the extremity of the cylinder 2 opposite the partition 3. The flanges or circular plates 7 and 8 are shaped in such a way as to allow one to simply pull on the plate or flanges 7 without being hindered by the other plate or flange 8, thus ensuring a grip that allows the fingers to push the piston 4 by means of the rod 6.

Conventionally, radial wings are attached to the rod 6, for example three or four wings, that start at this rod 6 and come into sliding contact into the inner wall of the cylinder 2 to ensure that the piston 4 does not slant and remains perpendicular to the axle of the cylinder during its shift.

Such syringes are either manufactured in a sterile environment or they are sterilized during the last stage of their production. They are sold wrapped, the piston 4 being completely pushed down to come in contact with the partition 3. Different types of gaskets 9 can ensure the tightness between the piston 4 and the inside of the cylinder 2. The gaskets have any suitable form, for example U-shaped gaskets, or quite simply, the friction between the plastic material composing both the piston 4 and the cylinder 2 will ensure a tight fit.

In this manner, during use, the piston 4 will be separated from the partition after a needle or catheter has been attached to the tip 5 and the compartment 1 will be gradually filled by either the injection or the sample liquid. In order to avoid errors in handling, there is usually provided a retaining ring (not shown) that limits the movement of the piston 4 to the inside of the cylinder 2, this retaining ring being positioned in such a way that the compartment 1 will hold a predetermined volume, for example five or ten cubic centimeters, when the piston 4 falls against the retaining ring.

A whole range of disposable syringes are usually marketed together, each syringe having a determined capacity. For the praticioner, doctor, or nurse, the prior art design results in the necessity of having at their disposal a relatively large stock of syringes corresponding to the injections or the sample taking that they are likely to perform between two purchases. This drawback is particularly evident in the case of those doctors, nurses or veterinarians who go on rounds and are obliged to load themselves up with a large number of syringes in order to face all the situations which they can find themselves confronted with during their day. The drawback is, of course, even more pronounced for those doctors and nurses who must go on long stays in the bush without being resupplied for relatively long periods of time.

Another drawback of the conventional syringes as shown in FIG. 1 is that, as we see in the figure, the volume of the injection or sample is limited by the diameter of the cylinder and the passage of the piston. For those syringes that hold a large capacity, for example one hundred cubic centimeters or more, it is already a matter of syringes of considerable diameter for which the passage of the piston is long, rendering the syringes cumbersome, difficult to manipulate, and not convenient for the syringue-pusher devices.

An object of the invention is to provide for syringues overcoming the drawbacks of the prior art.

For achieving this objective and others, this invention provides for a double compartment syringe comprising a first compartment constituted of a first cylinder that is closed off at one extremity by a first partition in which an opening with a tip is provided, and at its other extremity by a first sliding piston. This syringe also includes a second cylinder, coaxial to and inside of the first cylinder, attached at its first extremity to the first piston and closed off at its second extremity by a second partition, and an axial rod coaxial to and inside of the second cylinder, attached to the first partition at its first extremity. This axial rod slides accross the first piston and supports a second piston at its other extremity that slides into the second cylinder; whereby a second compartment opposite the first one is formed by the second cylinder, the second piston, and the second partition, the volumes of these two compartments fluctuating simultaneously when the second cyliner is shifted in relation to the first one.

To remedy the first drawback, the second partition of this syringe comprises an opening with a tip. Thus, the praticioner can attach the needle or the catheter to one or the other of the tips of either the first or the second compartment and inject one or the other of the two given liquids.

To remedy the second drawback and to obtain a syringe with a larger capacity with less hindrance, a connecting means has been designed to link the first and the second compartment.

In one embodiment, the connecting means is constituted of an opening that traverses the first piston and extends into the wall of the second cylinder.

In a more detailed embodiment of this invention the second cylinder comprises third and fourth concentric cylinders, the third cylinder, outside, being attached at one end to the first piston and being closed at the other end by the second partition, the fourth cylinder, inside, being also attached to the first piston, and openings being provided in the first piston at the level of the rim defined by the third and the fourth cylinder, and in the fourth cylinder in proximity to the second partition.

This syringe, in which the first and second compartments are connected, allows, for the same external bulk, a syringe with an approximately doubled capacity to that of a conventional syringe.

Figure 2:
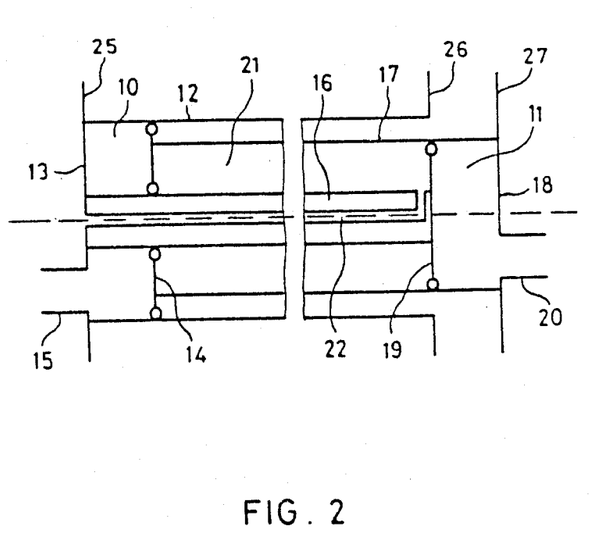
FIG. 2 is an extremely schematic representation of a syringe according to a first embodiment of this invention.

These objectives, features, and advantages as well as others of this invention will be exposed in further detail in relation to the following description of specific embodiments corresponding to the attached drawings, wherein:

FIG. 2 shows a syringe with two compartments according to this invention, wherein the two compartments are independent. This syringe can be used to either inject or sample one or the other of two different liquids depending on which compartment is used.

FIG. 2 shows the syringe according to this invention with a piston in the intermediate position. This syringe comrises a first compartment 10 and a second compartment 11. The first compartment 10 is bounded by a first cylinder 12, a first end partition 13 and a first piston 14. An opening with a tip 15 is provided for on the partition. A needle or a catheter used for either injections or for sample taking can be attached onto this tip.

Located substantially centrally inside the first cylinder 12 is an axial rod 16 having approximately the same length as the first cylinder 12 and attached to the first partition 13 at right angles. The piston 14, located opposite from the first compartment 10, is attached to a second cylinder 17 that is inside the cylinder 12. The length of this cylinder is such that, when the piston 14 is pushed down completely into the first compartment 10, the cylinder 17 projects slightly to the outside of the first cylinder 12. The second cylinder 17 is closed off by a partition 18.

At the extremity of the syringe opposite the first compartment 10, the second compartment 11 is defined by the second cylinder 17, the partition 18 and a piston 19 that is attached to the extremity of the axial rod 16. The piston 19 is fixed to the first cylinder 12 and is attached in such a way that it can slide tightly inside the second cylinder 17 when this cylinder is moved in relationship to the first cylinder 12. The second cylinder 18 comprises a tip 20 analog to tip 15 (or tip 5 of FIG. 1).

The two compartments 10 and 11 will have different capacities which will be in accordance with the diameters chosen for the cylinders 17 and 12. Compared to the conventional syringe of the same bulk, one will note that the first compartment 10 has a volume that is lightly inferior to that of the second compartment due to the presence of the axial rod 16. This difference in volume, however, is very slight.

In addition, one will notice that there appears to be a third compartment 21 bordered by the backs of the pistons 14 and 19 and the inner wall of the second cylinder 17. This third compartment has no active role in the functioning of the syringe and its volume is reduced substantially to zero when either the first or the second compartment of the syringe is filled. However, if this compartment is kept airtight when the syringe is being filled, that is to say when the second cylinder 17 is being pulled, excessive pressure acts against the traction. To avoid this problem, a canal 22 can be designed on the inside of the axial rod 16, one extremity of this canal opening to the outside across from the partition 13, the other extremity opening inside the third compartment near the second piston 19. Of course, several openings can be designed, for example three openings at 120° for creating a passageway between the canal 22 and the third compartment 21.

In FIG. 2, the small circles represent the points where the pistons form a sliding and tight contact with the walls of the first and the second cylinders, and with the surface of the axial rod. As this is standard pratice, these tight seals can be ensured by using various types of gaskets, or quite simply by the proper design of the plastic components themselves.

When using the syringe of this invention the practitioner can grasp the syringe by the flanges 25 protruding from the first cylinder that is found next to the first partition, by the flanges 26 protruding from the opposite side of the first cylinder, and by the flanges 27 protruding from the second cylinder that is found next to the second partition.

Figure 3:
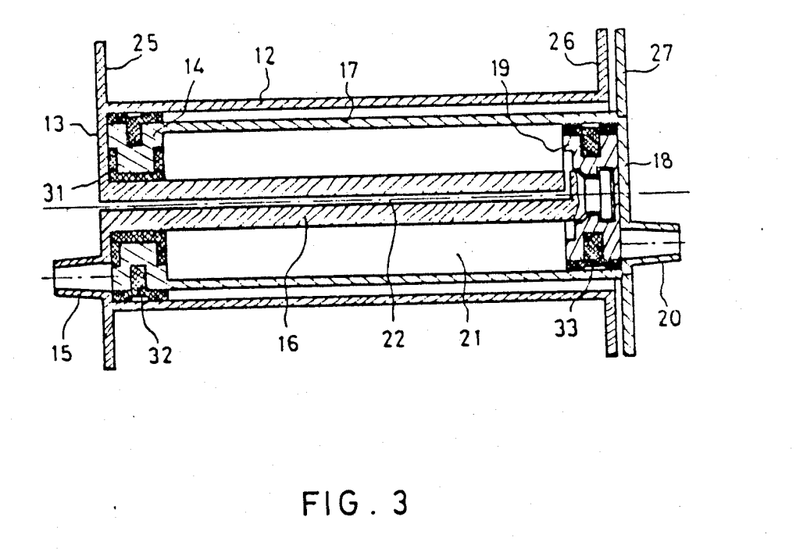
FIG. 3 represents a more detailed embodiment of the syringe of FIG. 2.

FIG. 3 represents a detailed implementation of the first embodiment of this invention. In this illustration, the same components are designated by the same numbers as in FIG. 2. The design of the pistons 14 and 19 are particularly noteworthy. Piston 14, integral with the second cylinder 17, supports an interior gasket 31 and an exterior U-shaped gasket 32. The second piston 19, also supporting a gasket 33, is attached by a ratchet mechanism to the extremity of the rod 16. The special design of both the openings and the external gasket 33 of piston 19 are noteworthy. The openings serve as vents, forming a link with the canal 22. The external gasket 33 is U-shaped. The ratchet mechanism facilitates the assembly of the components. In addition, one will note that the partitions can be affixed to the respective cylinder by either casting or gluing.

Figure 4:
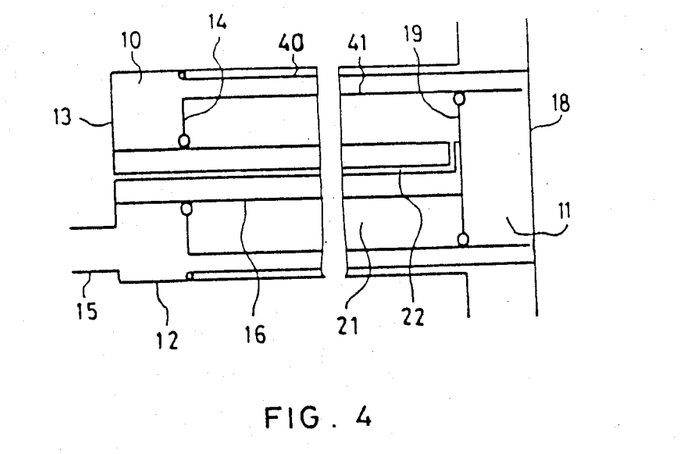
FIG. 4 shows an extremely schematic syringe according to a second embodiment of this invention.

FIG. 4 represents a second embodiment of this invention. The syringe, as it is designed in this embodiment, has a filling capacity that is approximately double to that of a standard syringe. As in FIG. 2, there are a first 10 and a second 11 compartment. In this embodiment, the second compartment 11 is not an isolated compartment that permits injections or sample taking of a given quantity of a liquid separately from the first compartment 10, but rather it is connected with the first compartment to create a composite compartment of approximately doubled volume.

In this second embodiment there are again the external cylinder 12, the first partition 13, the first piston 14, the tip 15, the axial rod 16, the second partition 18, the second piston 19, the third compartment 21, and the canal 22 that is provided in the axial rod 16. However, there is no tip 19, and the second cylinder 17 has been modified. This cylinder 17 has been replaced by two concentric cylinders 40 and 41, cylinder 40 having a diameter which is slightly inferior to that of cylinder 12 and cylinder 41 having a diameter slightly inferior to that of cylinder 40. Each one of these cylinders is attached to the first piston 14 in which openings are designed at the level of the circular rim defined by the cylinders. Cylinder 40 is also attached along its circumference to the partition 18 whereas cylinder 41 is not. This results in a connection between the first and the second compartments. Thus, when the partition 18 is slid towards the outside in order to increase the volume of both the first 10 and the second 11 compartment, the liquid comes back through the tip 15 and fills the two compartments, in this way approximately doubling the capacity of the syringe.

Figure 5:
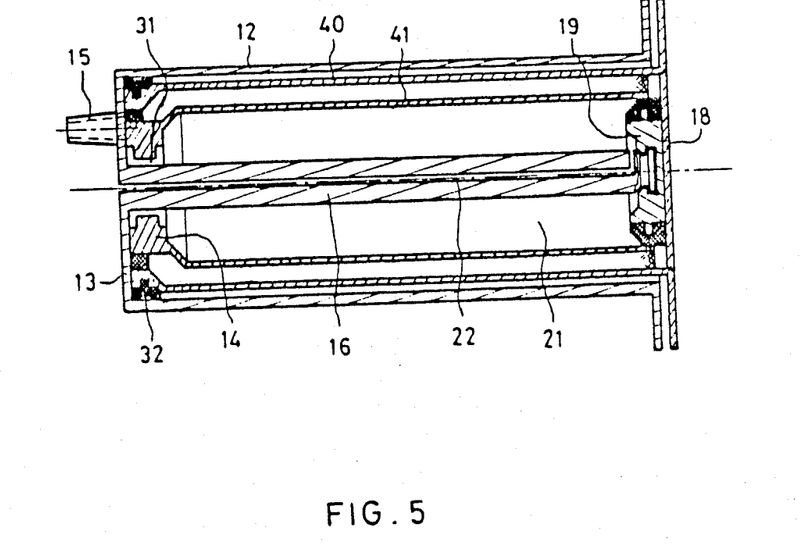
FIG. 5 represents a more detailed embodiment of the syringe of FIG. 4.

FIG. 5 is a more detailed representation of an implementation of the second embodiment of the invention. One will note, as in FIG. 3, the presence of fitted gaskets, their form also being different than that of the gaskets in FIG. 3. One will also note the specific design of the openings in the first piston, for ensuring a certain mechanical strength.

Other variants of the second embodiment of this invention would be possible as long as there is a passage that crosses the first piston and emerges in the second compartment, thus ensuring a connection between the two compartments that would allow them to be filled simultaneously.

Figure 6:
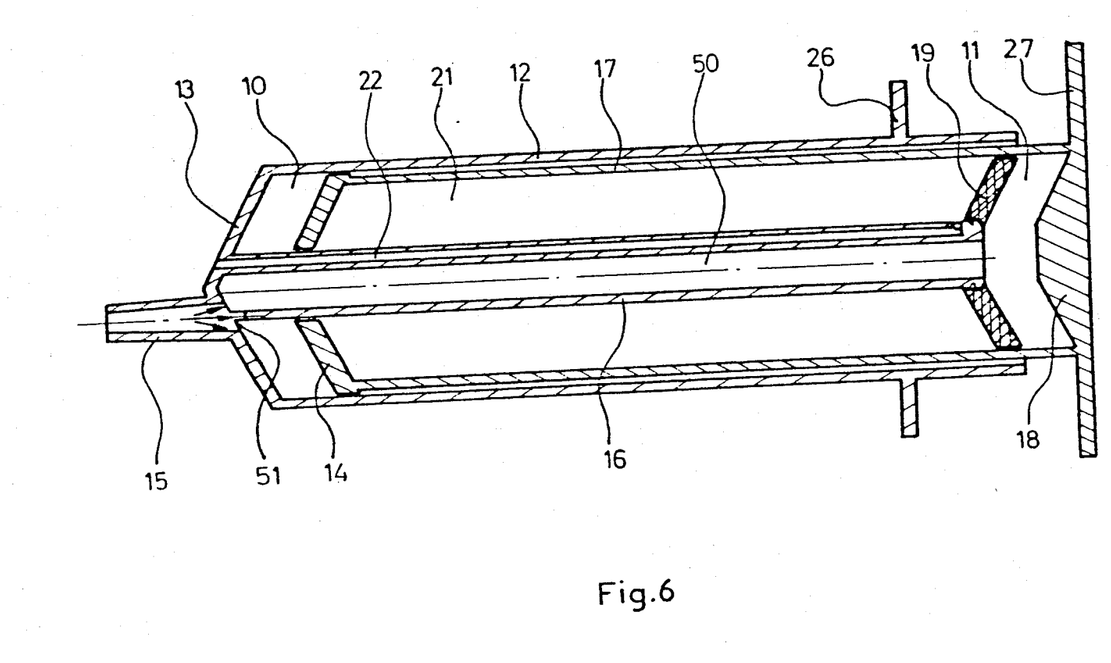
FIGS. 6 to 8 show various modifications of the second embodiment of this invention.

An example of such another variant is shown in FIG. 6. In this variant, as in the first embodiment, There are again the external cylinder 12, the first partition 13, the first piston 14, the tip 15, the axial rod 16, the second partition 18, the second piston 19, the third compartment 21, and the canal 22 that is provided in the axial rod 16. However, there is no tip 19, and the rod 16 has been modified and comprises, in addition to the vent canal 22, a canal 50 connecting the first and second compartments. This canal 50 replaces the passage way carried out by the two concentric cylinders 40 and 41 in FIGS. 4 and 5. The connection between the canal 50 and the compartment 11 is due to the fact that the first end of the canal opens towards compartment 11. The connection between canal 50 and chamber 10 is carried out through a lateral opening in this canal close to the tip 15. Additionally, as shown, the tip 15 can be arranged for communicating directly with both canal 15 and compartment 10. In fact, either of this communication would be sufficient in other embodiments.

In the embodiment of FIG. 6, no specific gaskets are provided, the tightness resulting from the contact between the plastic material of the elements. In a practical embodiment, the first compartment can have a capacity of 28 cc and the second compartment capacity of 24 cc, that is a total of 52 cc for a syringue having the size of a classical 25 cc syringue.

Figure 7:
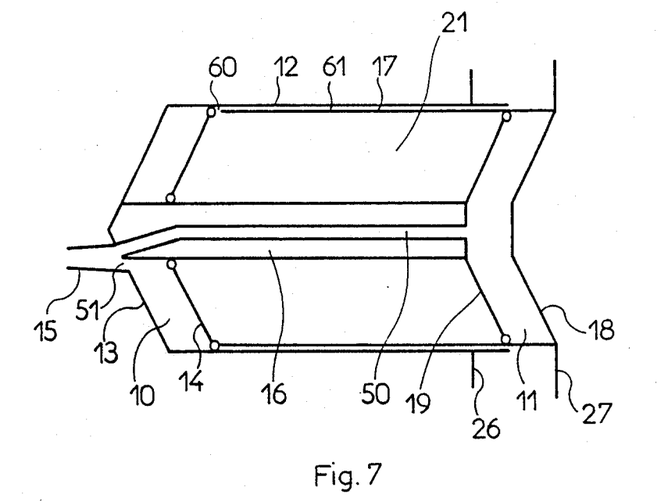
Figure 8:
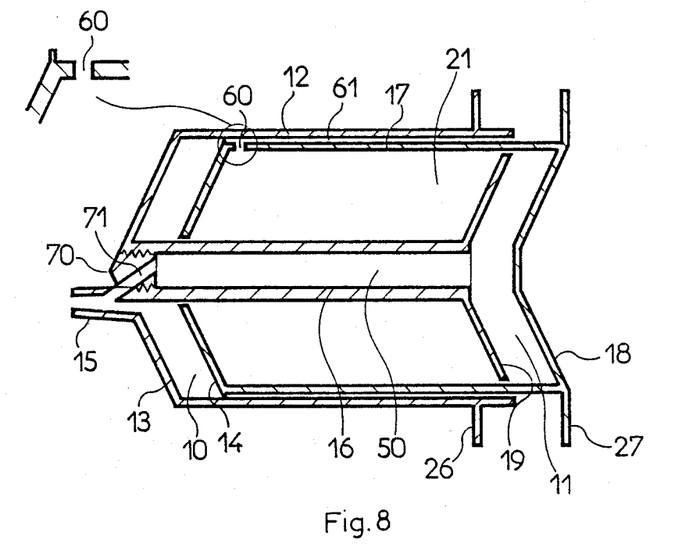

FIGS. 7 and 8 show other variants of the second embodiment. The largest part of those Figures is similar to FIG. 6 and the same references are used.

In FIGS. 7 and 8, the vent opening of the third chamber 21 is modified. Instead of a canal 22 in the rod 16, at least one radial aperture 60 crosses the wall of the second cylinder 17 close to the first piston 14. Thus an air inlet and/or outlet in the chamber 21 is possible through the apertures 60 and the separations 61 between the first cylinder 12 and the second cylinder 17. The manufacturing of the rod 16 is therefore easier.

FIG. 8 shows another mounting method for the rod 16 onto the partition 13. When manufacturing the partition 13 or the set including this partition, a pin 70 is fixed to or integrally formed with this partition. Thus the bored rod 16 is ratched, threaded, and/or sticked to this pin. As shown in FIG. 8, the pin 70 is provided with a canal 71 for communicating the bore 50 of the rod 16 and the chamber 11.

Of course, the diverse variations conventionally adopted for standard syringes can be adopted for the syringes of this invention. For example, a special means of centering such as wings could be included in the design to ensure that the movement of the various components closely follows the axis of the syringe. In the same way, the flanges or gripping device could have any standard shapes.

Another variant of this invention, based on the second embodiment corresponding to FIGS. 4 and 5, would consist of making the passage between the first compartment 10 and the second compartment 11 selectively closable. One would then be able to selectively use the syringe as: (1) a syringe of standard capacity by using only the first compartment 10, the passage between the compartments being closed off, (2) a syringe of doubled capacity, the first 10 and the second 11 compartments being connected, or (3) a syringe with two different capacities, the second compartment 11 being fitted with an opening and capable of being used in place of the first compartment 10 as in the first embodiment. This selective obturation could be achieved by lining up additional openings provided on discs or cylinders affixed on the parts of the syringe, which could then be selectively pivoted to attain the desired obturation.

In another variant of the first embodiment of this invention, the rod 16, instead of being attached to the partition 13 as shown in FIG. 2, would slide across this partition. The head of this axial rod, outside of the partition 13, is equipped with gripping and clamping devices, allowing the axial rod to be either attached to the partition 13 (this corresponds to the embodiment of FIGS. 2 and 3) or released from the partition. The rod 16 being released, it is possible to fill the second compartment 11 by creating traction on this axial rod, in keeping the volume of the first compartment 10 at its minimum. Next, it is possible to fill the first compartment 10 by relative displacement of the cylinders 12 and 17. The head of the rod 16 is then situated at the level of the partition 13 and can again be affixed to this partition. A relative displacement of the cylinders 12 and 17, by means of pressure, allows a simultaneous evacuation of the two compartments in draining volumes of liquid which are constantly proportional.

This last variant can find applications in complex chemotherapy in which there is a need to inject a mixture of drugs. In this case, the catheters at the tips of the two compartments will be connected to facilitate mixing the contents of the two compartments. The expert engineer will notice that it would be advisable to set the position of the openings 15 and 20 on top of the partitions 13 and 18; these openings could, for example, be set at the level of the extremities of the walls of the cylinders 12 and 15, respectively. Tips with either a simple or double bend could be designed so that the catheters to be attached are pointed in the same direction.

We claim:
1. A double compartment syringe comprising:
a first compartment (10) for containing a first volume of a fluid and defined by a first cylinder (12) closed off at a first extremity by a first partition (13) in which an opening (15) is provided for suctioning and expelling a fluid into and out of said first compartment (10), a second extremity of said first compartment defined by a first sliding piston (14) having an axial void therethrough;
a second cylinder (17, 40, 41) coaxial to and inside of the first cylinder (12), attached at a first end to a first surface of said first sliding piston (14) opposite said first partition (13), said second cylinder (17, 40, 41) closed off at a second end opposite said first end thereof by a second partition (18), said second partition having an opening opposite said first partition opening (15);
an axial rod (16), coaxial to an inside of the second cylinder (17, 40, 41) and engaging said axial void of said first sliding piston (14), said axial rod (16) attached to the first partition (13) at its first extremity, sliding within said axial void of the first piston (14) and supporting at its other extremity a second piston (19) that slides into the second cylinder (17, 40, 41), whereby a second compartment (11) opposite from the first compartment for containing a second volume of a fluid is defined by the second cylinder (17, 40, 41), the second piston (19) and the second partition (18), the volumes of said first and second compartments fluctuating simultaneously when the second cylinder (17, 40, 41) is shifted in relation to the first cylinder (12); and an opening (20) in the second partition (18) opposed to the opening (15) in said first partition (13) for suctioning and expelling fluids into and out of said second compartment.

2. A double compartment syringe comprising:
a first compartment (10) defined by a first cylinder (12) closed off at one extremity by a first partition (13) in which a first opening (15) is provided for injecting and aspirating fluids out from and into said first compartment, said first compartment defined at its other extremity by a first sliding piston (14), said first sliding piston having an axial central void therethrough;

a second cylinder (17, 40, 41) coaxial to and inside of the first cylinder (12), attached at one end to the first sliding piston (14) and closed at the other end by a second partition (18);

an axial rod (16), coaxial to and inside of the second cylinder (17, 40, 41), attached to the first partition (13) at its first extremity, sliding through said axial void of said first sliding piston (14), said axial rod supporting at its other extremity a second piston (19) that slides into the second cylinder (17, 40, 41), whereby a second compartment (11) opposite from the first compartment is defined by the second cylinder (17, 40, 41), the second piston and the second partition, the volumes of said first and second compartments fluctuating simultaneously when the second cylinder (17, 40, 41) is shifted in relation to the first cylinder (12); and fluid connecting means between the first and second compartments.

3. Syringe as claimed in claim 1 wherein a third compartment (21), made up of the space determined by the second cylinder and the first and second pistons, includes a vent means towards the outside atmosphere.

4. Syringe as claimed in claim 3 wherein said vent means comprise a canal (22) provided in said rod, emerging at one end through the first partition (13), and at the other end emerging in the third compartment (21) near the second piston (19).

5. Syringe as claimed in claim 2 wherein said connecting means comprises a canal (50) in said rod (16), said canal comprising at an end an aperture towards the second chamber and at its other end an aperture towards the first chamber and/or the second opening.

6. Syringe as claimed in claim 1 wherein said connecting means comprises an opening that crosses the first piston (14) and extends from the inner wall of the second cylinder to the second compartment (11).

7. Syringe as claimed in claim 6, wherein the second cylinder is composed of a third (40) and a fourth (41) concentric cylinder, the third external cylinder (40) being attached at one end to the first piston (14) and being closed off at the other end by the second partition (18), the fourth internal cylinder (41) being also attached to the first piston (14) and openings being provided in the first piston at the level of the rim formed by the third and fourth cylinders, and
in the fourth cylinder near the second partition.

8. Syringe as claimed in claim 1, further comprising gripping device, or flanges, which are designed at the outer circumference of the open extremity of the second cylinder and of at least one of the extremities of the first cylinder.

9. Syringe as claimed in claim 1 wherein said rod (16) slides across the first partition (13) and includes an external head equipped with gripping and clamping devices for optionally attaching said rod to said partition.

10. A double compartment syringe for injecting and aspirating fluids from either end thereof, said syringe comprising:
an outer syringe defining one of said compartments and including a barrel, an end wall closing a first end of said barrel, said end wall having a flanged opening therethrough for injecting and aspirating liquids into and out from said first compartment, an axial rod affixed at one end to an inner surface of said end wall, and a plunger having an axial void therethrough, slidably engaging said axial rod and having a peripheral surface in sliding contact with an inner wall of said barrel; and
an inner syringe defining the second of said compartments and including a barrel coaxially positionable within said outer syringe barrel and affixed to a surface of said outer syringe plunger opposite said outer syringe end wall, a inner syringe end wall closing an end of said inner syringe barrel opposite said outer syringe end wall, said inner syringe end wall including a flanged opening therethrough for injecting and aspirating liquids into and out from said second compartment, and a piston attached to said outer syringe axial rod in sliding contact with an inner wall of said inner syringe barrel.

11. A double compartment syringe having increased volumetric capacity for injecting and aspirating liquids, including
an outer barrel defining a first compartment;
an end wall closing a first end of said outer barrel;
a flanged opening in said outer barrel end wall for suctioning and aspirating liquids into and out of said first compartment;
an axial rod attached at one end to said outer barrel end wall;
a first piston attached to the other end of said axial rod; and
a fluid fillable piston handle defining a second compartment, including:
a piston handle end plate;
a second piston having an axial void therethrough slidably engaging said axial rod, a peripheral surface of said second piston in slidable contact with an inner wall of said outer barrel;
a first inner barrel coaxial with, and slidably positionable within, said outer barrel, one end of said first inner barrel attached to said second piston forming a fluid seal therebetween and the opposite end attached to said piston handle end plate forming a fluid seal therebetween;
a second inner barrel coaxial with and located within said first inner barrel, said second inner barrel being shorter than said first inner barrel, one end of said second inner barrel attached to said second piston forming a fluid seal therebetween, said second inner barrel being slidably positionable with said first inner barrel within said outer barrel, an opposite end of said second inner barrel spaced apart from said piston handle end plate thereby allowing fluid to communicate between said first and second inner barrels, said second piston having through holes in a portion thereof located between points of attachment of said first and second inner barrels thereby allowing fluid to communicate between said outer barrel of said first compartment and said fluid fillable piston handle of said second compartment.

* * * * *